(12) United States Patent
Scheckel

(10) Patent No.: US 8,864,642 B2
(45) Date of Patent: Oct. 21, 2014

(54) HOUSING FOR A FUNCTIONAL ELEMENT

(75) Inventor: Mario Scheckel, Berlin (DE)

(73) Assignee: ECP Entwicklungsgesellschaft mbH, Berlin (DE)

( * ) Notice: Subject to any disclaimer, the term of this patent is extended or adjusted under 35 U.S.C. 154(b) by 266 days.

(21) Appl. No.: 13/146,452

(22) PCT Filed: Feb. 11, 2010

(86) PCT No.: PCT/EP2010/000965
§ 371 (c)(1),
(2), (4) Date: Oct. 11, 2011

(87) PCT Pub. No.: WO2010/091900
PCT Pub. Date: Aug. 19, 2010

(65) Prior Publication Data
US 2012/0041254 A1    Feb. 16, 2012

Related U.S. Application Data

(60) Provisional application No. 61/151,964, filed on Feb. 12, 2009.

(30) Foreign Application Priority Data

Feb. 12, 2009  (EP) .................................... 09075071

(51) Int. Cl.
*A61M 1/10*  (2006.01)
*A61M 1/12*  (2006.01)
(52) U.S. Cl.
CPC ............. *A61M 1/101* (2013.01); *A61M 1/1024* (2013.01); *A61M 1/125* (2013.01)
USPC .......................................................... 600/16

(58) Field of Classification Search
USPC ............. 600/16–18; 623/3.1, 1.16, 1.28, 1.49
See application file for complete search history.

(56) References Cited

U.S. PATENT DOCUMENTS

2004/0044266 A1* 3/2004 Siess et al. ...................... 600/16
2004/0210304 A1* 10/2004 Seguin et al. ................. 623/2.11
2008/0132748 A1   6/2008 Shifflette

FOREIGN PATENT DOCUMENTS

| DE | 10 2004 054714 | 5/2006 |
| WO | WO 94/05347 | 3/1994 |
| WO | WO 03/103745 | 12/2003 |

OTHER PUBLICATIONS

International Preliminary Report on Patentability, from PCT/EP10/000965, mailed Aug. 28, 2011.
International Search Report and Written Opinion, from PCT/EP10/000965, mailed May 17, 2010.

* cited by examiner

*Primary Examiner* — Amanda Patton
(74) *Attorney, Agent, or Firm* — Marshall & Melhorn, LLC

(57) ABSTRACT

The invention relates to a housing (8) for a functional element (5), in particular for use in the medical field in naturally occurring vessels in the body, the housing wall of which has a slack, flexible, tensionable membrane (8a) with a plurality of formed parts (8b, 8c) secured thereon which support the membrane in the tensioned state thereof. Hence the housing can be expanded and compressed easily, the membrane being supported effectively in the expanded state by formed parts.

20 Claims, 4 Drawing Sheets

Figure 1:
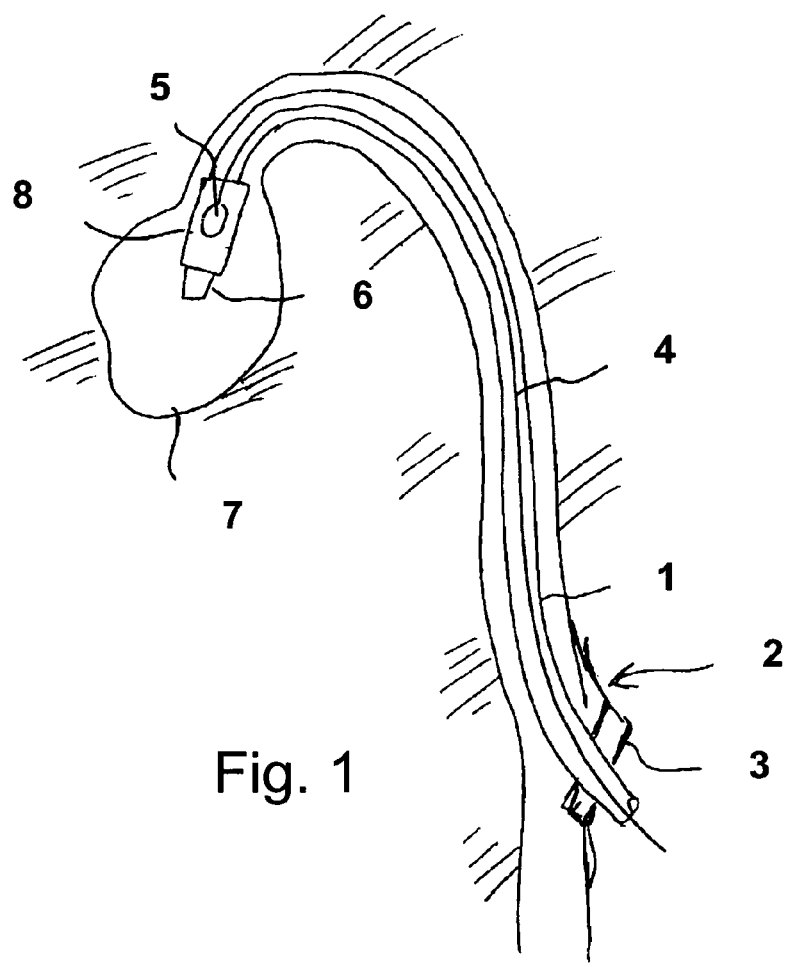

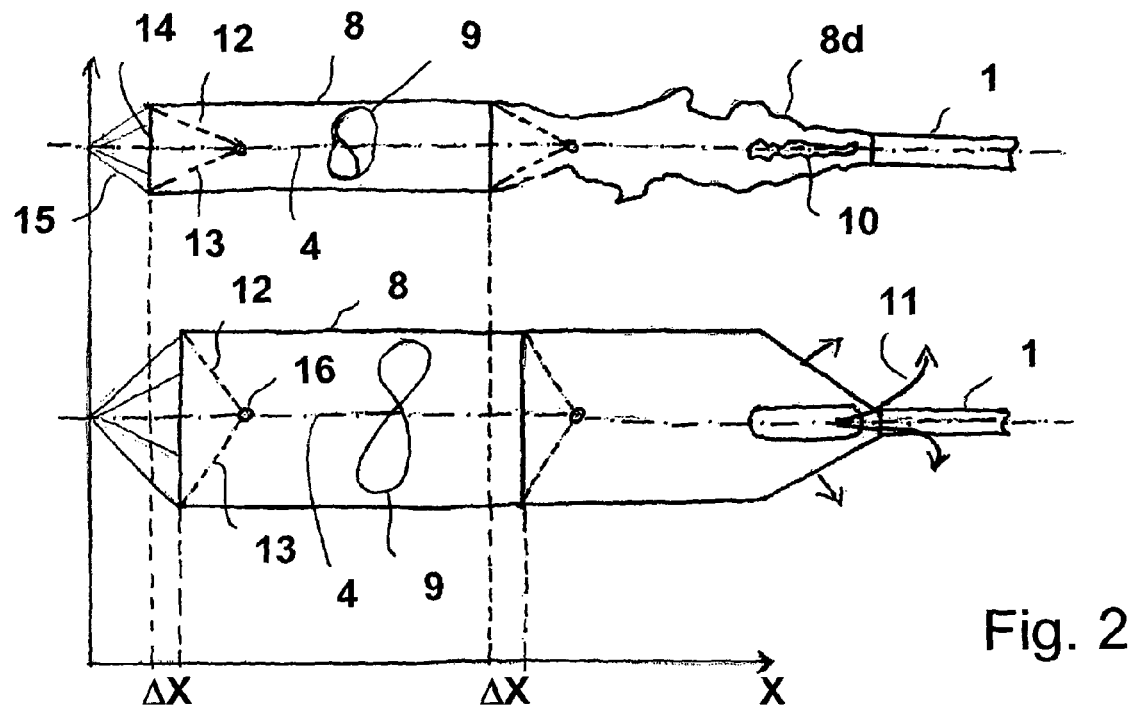
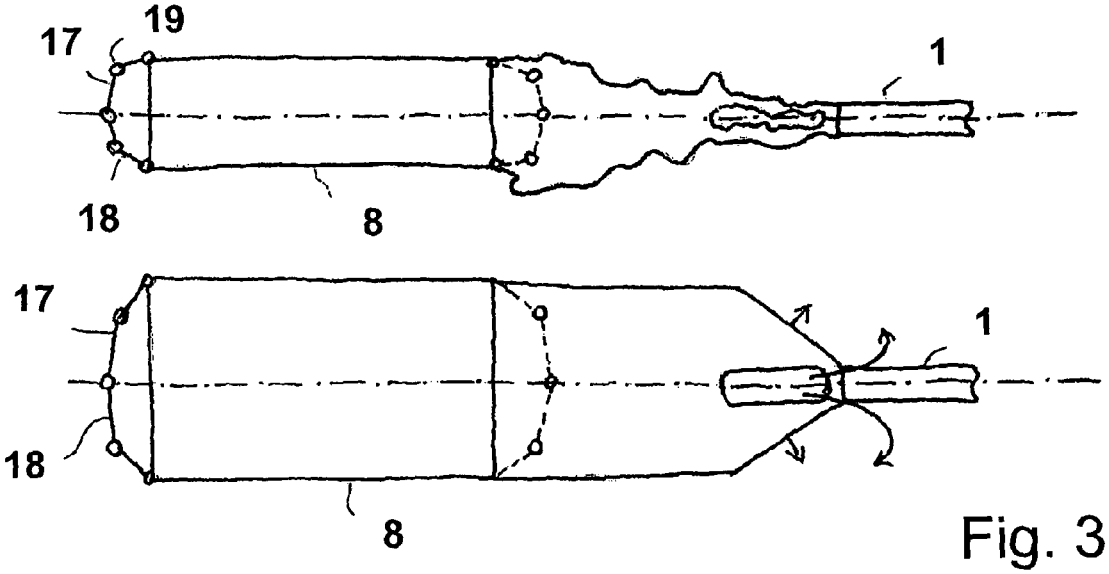
Fig. 2
Fig. 3

HOUSING FOR A FUNCTIONAL ELEMENT

The invention resides in the field of mechanical engineering and precision engineering and can be used advantageously in particular in the medical field.

In particular in the field of medicine, high demands are placed upon housings for functional elements which are used for example in invasive or micro-invasive operations. Such housings must often be very small just as the corresponding functional elements in order as far as possible not to cause damage during introduction into the body of a patient or to require small incisions. Micro-invasive operations are thus possible in order to assist for example bodily functions, such as blood circulation, i.e. the pumping capacity of the heart, or similar.

In particular for micropumps which can be operated in the body of the patient, pump housings which can be introduced into the body with the respective pump via a blood vessel are known. For this purpose, often both the pump blades of the pump and the pump housing are deformable between a compressed state for movement through a body vessel and an expanded state in which the pump is operated according to plan.

Various approaches to this are known from the literature, as to how components of this type can be compressed or expanded in the body in a controlled manner. It is known for example to use so-called shape memory materials which can be brought into various shapes for example by temperature changes. However, it should be noted in conjunction with the use of shape memory materials that these often have non-linear mechanical properties which are partially difficult to control and in addition are cost-intensive.

A solution is known from the patent document DE 10 2004 054 714 A1, in which both the impeller of a micropump and the housing thereof is expanded by a relative axial displacement of the pump drive shaft relative to a catheter. As a result, the housing is folded between the compressed and the expanded state.

From WO 00/2003103745 A2, a system in which the pump housing likewise is radially expanded by an axial relative movement of two components relative to each other is known.

DE 10 2004 054714 A1 teaches a blood pump with a flexible housing in the form of a hose that is supported by elastic sticks directed parallel to a rotor axis and extending each from the proximal end of the housing nearly to its distal end.

US 2008/0132748 shows a blood pump with a rotor that is moving in a rib cage housing formed by bendable ribs. The length of the ribs is comparable to the length of the housing. The ribs exhibit an arcuate shape and in the extended state of the housing it has an ellipsoidal or prolate-spheroid form.

WO 94/05347 describes a blood pump with a rotor that is placed in a housing that is provided with a lattice of bars in order to shield the rotor. The bars have the form of one-piece filaments extending in the longitudinal axis of the rotor. This filament cage can be expanded by displacement of the ends of the filaments.

Against the background of the state of the art, the object underlying the invention is to produce a housing which can be compressed or expanded with as simple means as possible, the constructional complexity requiring to be minimised. Nevertheless, the housing should have the stability required for operation.

The object is achieved according to the invention by the features of patent claim 1.

The invention relates to a housing for a functional element, in particular for use in the medical field in naturally occurring vessels in the body, the housing wall of which has a slack, flexible, tensionable membrane with a plurality of formed parts secured thereon which support the membrane in the tensioned state thereof by forming one or more groups of formed parts wherein the parts of each group support one another in the tensioned state of the membrane.

The separately formed parts allow for folding and compressing of the housing in all directions without substantial resistance forces.

For this purpose, the parts of a group may be in touching contact to other parts of the same group, when the membrane is in its tensioned state. The parts may abut against each other, engage one in the other or overlap each other. In the non-tensioned state of the membrane, they may or may not touch other parts of the same group.

All the components are advantageously configured for this purpose from biocompatible materials. The formed parts may be individually attached to the housing as separate bodies.

Advantageously, at least one group of formed parts forms a rib-like linear structure in the tensioned state of the membrane. The one or more rib-like structures may have straight or circular or semicircular form or arc form. These rib-like or arc-like structures may be directed parallel to a longitudinal axis of the housing.

The parts of at least one group may as well build a two-dimensional shield form that covers a part of the surface of the housing.

The corresponding formed parts are advantageously stable in shape and rigid and can be configured as injection moulded parts, in particular made of plastic material, and are essentially bar- or plate-shaped.

Furthermore, the invention can advantageously be configured in that at least one of the formed parts has a support surface which abuts against the membrane in the tensioned state.

Also a plurality of formed parts in the tensioned state can abut against the membrane flatly in an adjacent manner, in particular on the inside thereof, in order to form a covering of the membrane which supports the latter and does not impede a fluid flow within the housing.

The formed parts can advantageously be connected exclusively to the membrane, i.e. have no connection to a further component in the interior of the housing. The positioning of the housing with respect to a functional element, in particular a pump, can then be achieved by support arms which are described further on.

The formed parts can be connected rigidly by their entire support surface which abuts against the membrane or be connected also only to a part of the support surface, in particular to a delimiting edge of the support surface.

The connection of the formed parts to the membrane can be produced for example as an adhesive joint.

In the tensioned state of the membrane, the formed parts abutting against the inside of the housing/of the membrane can essentially cover the membrane and also abut against each other.

The membrane is consequently reinforced and protected effectively from damage from the inside.

The formed parts can partially overlap each other and as it were lie one above the other in the manner of scales or in the manner of shingles. Hence a particularly good support and gap-free covering of the membrane is ensured.

The formed parts can also partially engage one in the other in order to be mutually supported and positioned.

Hence the formed parts in the tensioned state of the housing can form an inherently stable support body which supports the membrane from inside.

The invention relates in addition also to a device having a housing according to the above-described type and having a functional element, the device having a fluid pump which produces an excess pressure in the housing which leads to tensioning of the membrane.

Hence the moveability of the slack, flexible membrane and the moveability of the formed parts in the non-tensioned state of the membrane is used for the purpose of tensioning the membrane by means of an excess pressure in the housing without a notable counter-force and for stabilising and supporting said membrane by means of the abutting formed parts in the tensioned state. If necessary, when starting up the pump if this is disposed in the housing, it must be accepted that the pump blades of the pump rub on parts of the housing until the housing is expanded according to plan by the excess pressure building up and a pump gap is configured between blade tip and housing.

If the pump is switched off again, then the housing collapses and can be retracted together with the functional element through the naturally occurring vessel in the body or an artificial vessel—e.g. a lock.

In contrast to other concepts for compressible and expandable housings, the compression movement of the housing, after stopping the pump, encounters no noteworthy elastic counter-force which would make the compression process difficult. The described behaviour when retracting into an artificial vessel and during transport through this vessel turns out to be particularly advantageous since little force need be expended hereby for the translatory movement through the vessel.

The expansion or compression of the housing, if a functional element different from a pump is disposed in the latter, can also be achieved in that the housing is subjected to pressure with an externally disposed fluid pump or the pressure is reduced for collapsing.

A typical application for the invention is the production with a blood pump so that, during operation, the pump conveys blood and hence builds up an internal pressure which expands the housing for example in a ventricle as desired.

If a fluid pump is located in the housing, then advantageously a suction opening and a catheter connection are provided. The suction opening can have for example a suction cage which, on the one hand, retains coagulated blood components away from the pump and, on the other hand, protects the naturally occurring bodily tissue outside the housing from injury by the pump blades if a rotor pump is used.

If the housing is used for a blood pump that works without a rotor and instead has a pulsatile pumping element, for example in the form of a cushion with variable volume, then the formed parts may support the membrane of the housing and at the same time, the parts are not endangered by the movement of a rotor while the housing is extending. Therefore, the housing may advantageously be used as housing of a pump with a drive element that comprises a cushion with variable volume. Usually, this pump concept requires appropriate valves in the openings of the housing that are controllable by a control unit.

Support arms advantageously serve to position and centre the housing relative to a functional element located in the latter, in particular a pump rotor. These can extend for example radially from the housing up to the functional element or possibly up to a drive shaft or a component mounted on the latter and be supported thereon at least one formed part and/or be secured on the membrane.

In the case where the radially inner end of the support arms is fixed in the axial direction, an axial movement of the housing results in the course of the compression/expansion movement at the same time if the support arms are not flexible or not provided with at least one bending joint.

The support arms can advantageously engage in the expanded state of the housing, the corresponding locking devices being intended to be configured such that bending of the support arms is effected as soon as the excess pressure in the pump housing falls below a specific threshold value.

Hence the support arms in the expanded state of the housing exert an additional support effect.

Even if each support arm is provided with a plurality of joints, these can engage in a stable manner at a corresponding angle which corresponds to the desired state in the expanded state of the housing until the housing collapses due to the lowering of the excess pressure. Then the support arms can bend to compress the housing.

The support arms can also form a suction cage at the same time in the inlet region of the housing in which a fluid is suctioned in.

Apart from a housing of the described type or a device with such a housing, the invention relates in addition also to a method for the production of a housing in which formed parts are secured firstly on a flat membrane and thereafter the membrane is rolled up and fitted together to form a hose.

In this way, the formed parts can be secured easily on the membrane in an automated method, for example by glueing, without spatial problems impeding this process. The housing is thereafter produced from the flat membrane as a hose which can advantageously taper conically at one of its ends to form a catheter connection. At the opposite end of the hose, support arms can be provided in order to form a suction cage.

In the following, the invention is shown in a drawing with reference to an embodiment and subsequently explained.

There are thereby shown

FIG. 1 basically the construction of a catheter with a heart pump introduced through a blood vessel into a ventricle, FIG. 2 in a side view, the housing in the compressed state (above) and in the expanded state (below), FIG. 3 a side view of another housing in the compressed state (above) and in the expanded state (below), FIG. 4 the housing in the compressed state in a cross-section, FIG. 5 the housing in a partially expanded state in a cross-section, FIG. 6 the housing in the expanded state in cross-section, FIG. 7 the housing in partially expanded state with an incorporated pump, FIG. 8 the housing in the expanded state with an expanded pump in a cross-section, FIG. 9 a three-dimensional view of the membrane in the flat state with formed parts glued on, and also FIG. 10 the formed parts on the membrane in the expanded state with a representation of the mutually engaging ends of the formed parts.

In a longitudinal section, FIG. 1 shows schematically a catheter 1 which is introduced into a blood vessel 2 of a human body by means of a lock 3 and is conveyed through this vessel into the ventricle 7.

A functional element 5 with a housing 8 is located at the end of the catheter 1, the functional element 5 comprising a blood pump with an impeller and the housing 8 having a suction cage 6 on its end.

A shaft 4 which extends up to the pump 5 and actuates the impeller there with the pump blades is provided within the catheter 1.

The housing 8 is shown in an at least partially expanded state which it assumes after introduction into the ventricle and the pump being set in operation.

The housing and the pump are described subsequently in more detail with reference to the remaining Figures.

In FIG. 2, a side view of the housing 8 is represented at the top in the compressed state, said housing being connected to the catheter 1 and receiving a pump impeller 9 in the likewise compressed state in its interior. The pump impeller can have for example a hub and pump blades folded onto the latter.

The housing 8 has a conically tapered part 8d which is connected to the catheter 1 and which has, in the region in front of the catheter, at least one opening 10 via which the liquid can flow out. This is represented by the arrows 11 for a plurality of openings. Hence the transport of the fluid from a location of lower pressure—in the ventricle—to a location in which the pressure is increased locally by the energy input of the pump—can be produced above the aortic sinus (sinus aortae). The aortic valve (valva aortae) situated in front of the opening 10 acts as valve and prevents the fluid from flowing back into the ventricle 7.

The housing 8 is constructed essentially cylindrically at least in the expanded state (at the bottom) and comprises, in its outer region, a membrane which is fitted on its inside with formed parts. The formed parts are dealt with further on in more detail.

FIG. 2 shows in addition support arms 12, 13 which, on the one hand, are secured on at least one point on the housing 8 and, on the other hand, on the shaft 4 which extends along the dot-dash line which in addition also represents the cylindrical axis of symmetry of the arrangement.

The support arms 12, 13 are folded in in the compressed state in the longitudinal direction of the shaft 4 and are located at an acute angle to the latter.

If the pump impeller 9 is set in operation so that the pump begins to rotate, then a flow is produced in that liquid from the surroundings of the housing 8 is suctioned into the opening 14 through a suction cage 15 and is accelerated towards the catheter 1. In the pump housing 8, an excess pressure relative to the surroundings which expands the pump housing 8 radially is hence produced. To the same degree as the pump housing 8 expands radially, the pump blades of the pump can be deployed and consequently the power of the pump can be increased.

In the lower part of FIG. 2, the housing 8 is represented in the fully expanded state, the pump impeller 9 also being fully opened out. In this state, the pump provides its full power and the support arms 12, 13 are spread relative to the shaft 4 at an obtuse angle.

In this state, the supports arms 12, 13 can engage for example at their articulation point 16 at a rigid angle so that they support the expanded state of the housing 8.

In the course of the expansion of the pump housing 8, also an axial movement/compression of the housing 8 by the amount ΔX takes place due to the spreading of the support arms 12, 13, as is indicated in FIG. 2.

A similar pump housing 8 as in FIG. 2 is shown in FIG. 3, the support arms 17, 18 differing from those shown in FIG. 2 in that each support arm has per se one or more joints 19.

These joints 19 effect a more flexible adaptation of the support arms 17, 18 to the degree of expansion of the housing 8 and lead to the axial compression/displacement of the housing 8 during the tensioning being reduced or eliminated.

Also the articulated support arms 17, 18 can engage in a specific position so that, even in this constellation, an additional supporting of the expanded housing is possible. The engaged position can be overcome during collapse of the housing 8 by applying a specific threshold force.

In addition, the constellation of FIG. 3 has the particular feature that the support arms 17, 18 curve outwards from the housing 8 towards the housing exterior so that the support arms can form at the same time a convenient suction cage 15.

Figure 4:
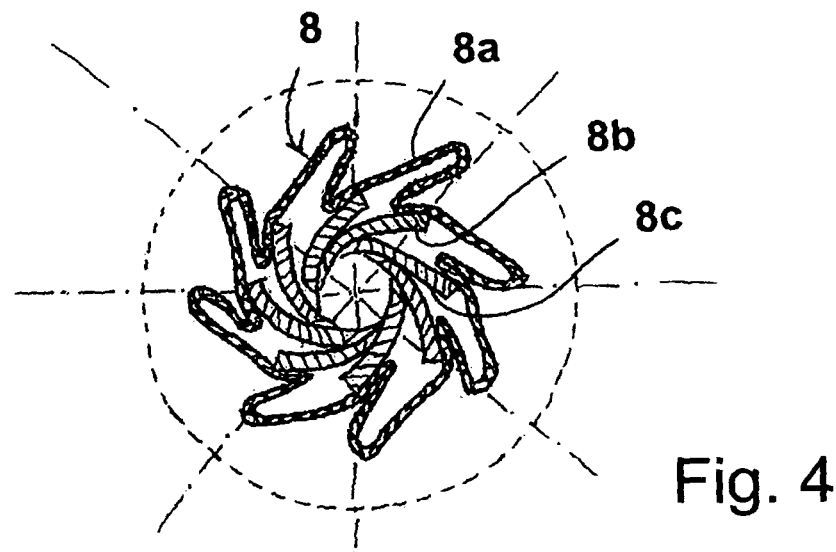

FIG. 4 shows, in a cross-sectional view, the housing 8 in the compressed state, it being clear in this representation that the housing 8 has a membrane 8a and formed parts 8b, 8c which are present folded together in the compressed state of the housing. The individual formed parts 8b, 8c are connected respectively merely in a partial region of their support surface 22 to the membrane 8a by glueing. The pump rotor is not illustrated in the representation of FIGS. 4, 5 and 6 for the sake of clarity.

Figure 5:
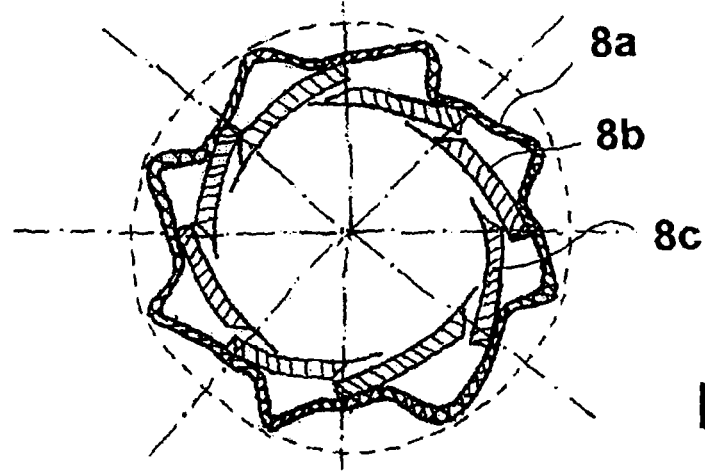

FIG. 5 shows the housing in a partially expanded state, the formed parts 8b, 8c approaching the membrane 8a with their support surfaces.

Figure 6:
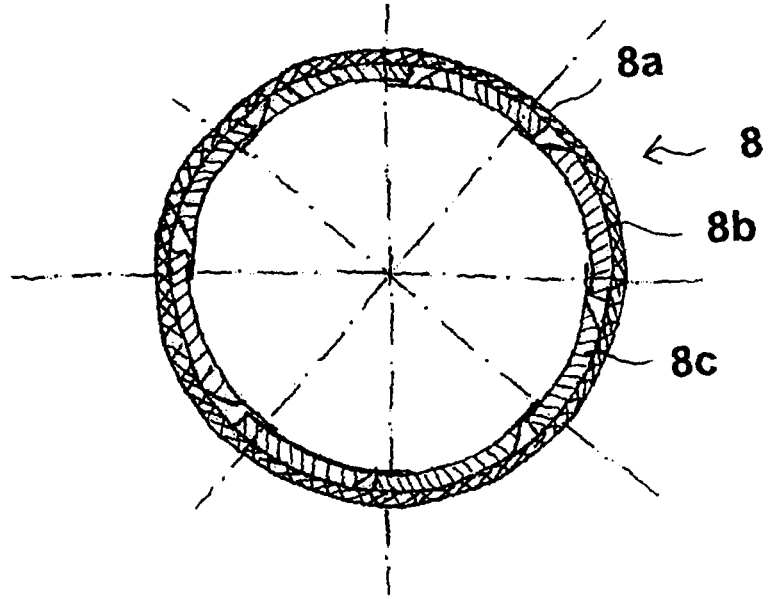

In FIG. 6, the housing 8 is shown in the completely expanded state, the formed parts 8b, 8c abutting completely against the membrane 8a and hence also not impeding a flow within the housing. In this state, the formed parts 8b, 8c mutually touch and overlap so that they mutually engage and mutually support their position. Hence, they form a scale-like reinforcement of the membrane and contribute substantially to the stability of the housing.

Figure 7:
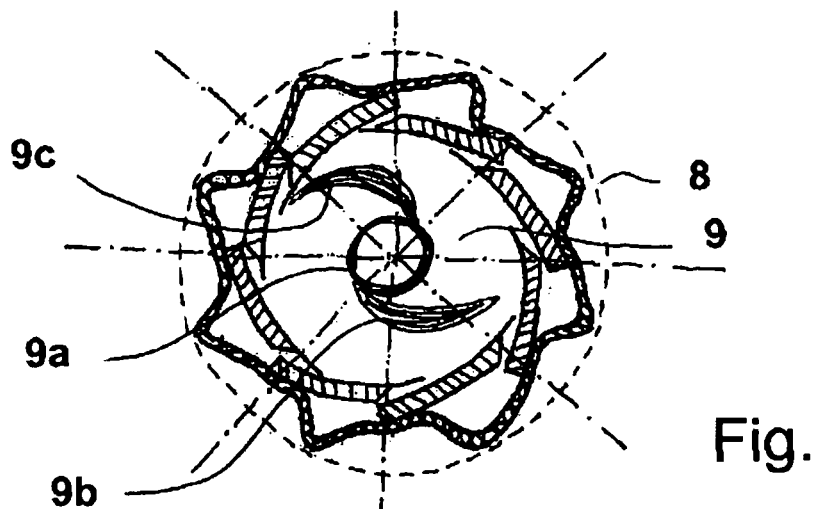

In FIG. 7, the pump housing 8 with a pump rotor 9 is represented in cross-section, the pump rotor 8 having a hub 9a and pump blades 9b, 9c. The pump blades 9b, 9c are folded against the hub 9a at least partially, which is made possible in that the pump blades are secured either in an articulated manner on the hub or are configured per se to be elastically flexible.

Figure 8:
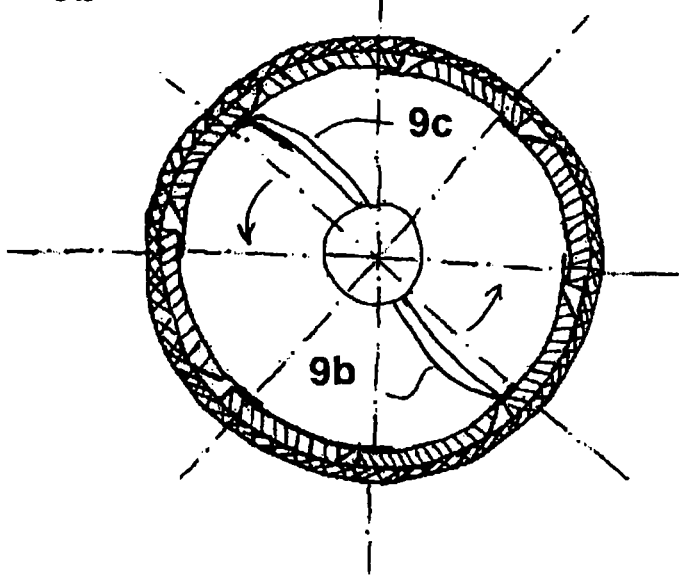

In the representation of FIG. 8, the housing 8 is completely expanded and the pump blades 9b, 9c are deployed to the maximum so that the maximum pump power is achieved in this constellation.

Figure 9:
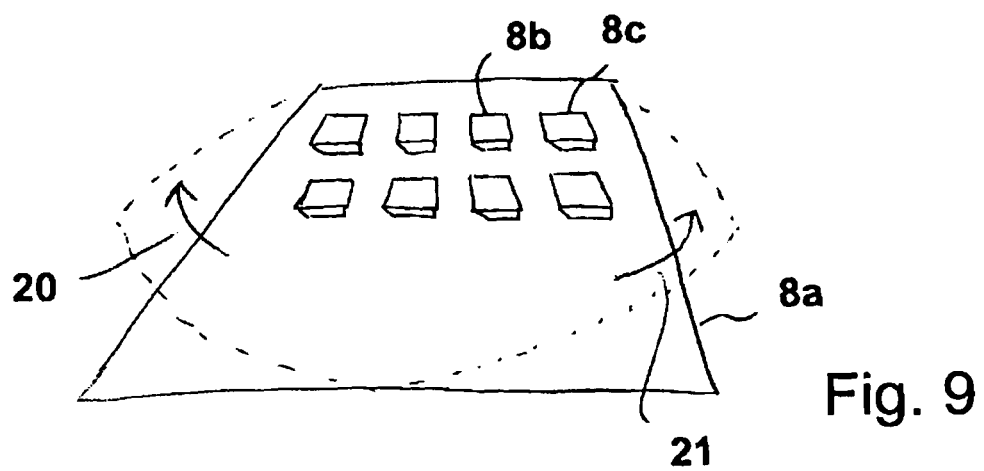

In FIG. 9, finally a flat membrane 8a is shown, on which formed parts 8b, 8c are secured by glueing before the membrane 8a, as indicated by the arrows 20, 2, is rolled up and fitted together to form a hose.

Figure 10:
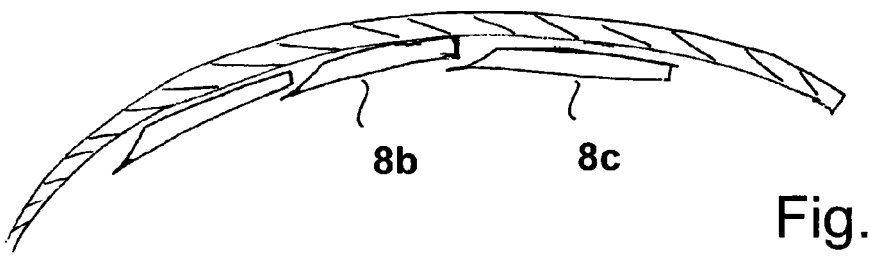

FIG. 10 shows, enlarged, the mutual engagement of formed parts 8b, 8c which have an asymmetrical configuration and are situated one above the other in a shingle- or scale-like manner.

As a result of this type of production, a housing according to the invention can be produced particularly easily and economically. The membrane can thereby be produced as a slack, flexible foil, elastically or non-elastically, and the formed parts 8b, 8c can be produced typically as plastic material injection moulded parts. The shingle- or scale-like positioning in the region of the formed parts 8b, 8c situated one above the other makes possible an advantageous compensation for the process-induced deviations in length and position of the formed parts. Greater production tolerances can be accepted and hence production costs can be lowered. An at least partially automated production is made possible.

The housing according to the invention hence makes possible simple expandability with low costs and low constructional complexity without external force expenditure, simply by producing a fluid pressure in the housing. This can be produced particularly easily when used with a pump. Even during compression of the housing, practically no counterforces are produced so that the housing possible with a catheter and possibly with a lock can be removed again easily from the body of a patient.

The invention claimed is:

1. A housing for a functional element, in particular for use in the medical field in naturally occurring vessels in the body, the housing wall of which has a slack, flexible, tensionable membrane with a plurality of formed parts secured thereon which support the membrane in the tensioned state thereof by forming one or more groups of formed parts wherein the formed parts of each group support one another in the tensioned state of the membrane, said formed parts of said groups positioned in a gap free relationship with respect to one another in said tensioned state, and a functional element comprising a fluid pump which produces an excess pressure in the housing which leads to tensioning of the membrane.

2. The housing according to claim 1, characterised in that at least one group of formed parts forms a rib-like linear structure in the tensioned state of the membrane.

3. The housing according to claim 1, characterised in that the formed parts are connected at least to the membrane.

4. The housing according to claim 1, characterised in that at least one formed part has a support surface which abuts against the membrane in the tensioned state.

5. The housing according to claim 3, characterised in that the at least one formed part is connected to the membrane on the entire support surface.

6. The housing according to claim 4, characterised in that the at least one formed part is connected to the membrane only on a part of the support surface, in particular only to a delimiting edge of the support surface.

7. The housing according to claim 4, characterised in that the formed part is secured on the membrane by an adhesive joint or another joining connection.

8. The housing according to claim 1, characterised in that the formed parts essentially cover the membrane in the tensioned state on the inside of the housing.

9. The housing according to claim 1, characterised in that adjacent formed parts abut against each other in the tensioned state.

10. The housing according to claim 9, characterised in that adjacent formed parts overlap each other partially in the tensioned state.

11. The housing according to claim 9, characterised in that adjacent formed parts engage one in the other in the tensioned state.

12. A device according to claim 1, characterised in that the pump forms the functional element.

13. A device according to claim 1, characterised by a suction opening and a catheter connection.

14. A device according to claim 1, characterised by a cushion with a variable volume that drives the fluid.

15. A device according to claim 1, wherein said fluid pump is a pump rotor having at least one pump blade located within said housing.

16. A device according to claim 15, characterised by support arms which support and/or centre the housing relative to the pump rotor or its shaft.

17. A device according to claim 16, characterised in that the support arms are flexible or bendable at least one bending joint.

18. A device according to claim 16, characterised in that the support arms engage in the tensioned state of the membrane.

19. Method for the production of a housing according to claim 1, characterised in that formed parts are secured firstly on a flat membrane and thereafter the membrane is rolled up and fitted together to form a hose.

20. A housing for a functional element, in particular for use in the medical field in naturally occurring vessels in the body, the housing wall of which has a slack, flexible, tensionable membrane with a plurality of formed parts secured thereon which support the membrane in the tensioned state thereof by forming one or more groups of formed parts wherein the formed parts of each group support one another in the tensioned state of the membrane to form a smooth cylindrical inner housing wall, and a functional element comprising a fluid pump which produces an excess pressure in the housing which leads to tensioning of the membrane.

\* \* \* \* \*